United States Patent [19]

Adger

[11] Patent Number: 4,677,228

[45] Date of Patent: Jun. 30, 1987

[54] CHEMICAL PROCESS

[75] Inventor: Brian M. Adger, Stamfordham, England

[73] Assignee: Smith Kline & French Laboratories, Ltd., Welwyn Garden City, England

[21] Appl. No.: 826,954

[22] Filed: Feb. 7, 1986

[30] Foreign Application Priority Data

Feb. 9, 1985 [GB] United Kingdom ................. 8503359
Jun. 8, 1985 [GB] United Kingdom ................. 8514550

[51] Int. Cl.[4] ............................................. C07C 103/34
[52] U.S. Cl. .................................................... 564/218
[58] Field of Search ........................................ 564/218

[56] References Cited

U.S. PATENT DOCUMENTS 2,206,911 7/1940 McNally et al. ............... 564/218 X
3,352,904 11/1967 Bicking et al. .................. 564/218 X
4,032,573 6/1977 Kaneko et al. ................. 564/218 X

OTHER PUBLICATIONS

McEvoy et al., A General Synthesis of 3-(Substituted Benzoyl)-3-Substituted Alkanoic Acids, J. Org. Chem., vol. 38, No. 23, pp. 4044-4048, (1973).

*Primary Examiner*—Paul F. Shaver
*Attorney, Agent, or Firm*—Mark R. Daniel; Janice E. Williams; Alan D. Lourie

[57] ABSTRACT

This invention relates to a Friedel-Crafts acylation process using trichlorobenzene as solvent.

11 Claims, No Drawings

CHEMICAL PROCESS

The present invention relates to an improved process for preparing phenylalkyl and phenylhaloalkyl ketones, and in particular where there is a para-alkanoylamino substituent on the phenyl ring. Such compounds are of the general formula (I):

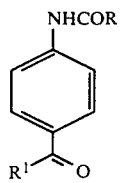
(I)

in which R is $C_{1-4}$alkyl; and $R^1$ is $C_{1-4}$alkyl or $C_{1-4}$haloalkyl. These compounds are useful intermediates for preparing pharmaceutical compounds, for example see McEvoy et al J. Org. Chem. 38 1973, p 4044.

Attempts have been made to prepare the compounds of the formula (I) by use of conventional Friedel-Crafts conditions. One method has been to react propionamidobenzene with aluminium chloride and propionyl chloride in a melt to give 40%–50% of recrystallised product. However on a commercial scale reaction in a melt is unsatisfactory. When acetanilide is reacted with propionyl chloride in a melt about 30% yields are obtained with production of undesirable isomers and further impurities.

When propionamidobenzene was reacted with propionyl chloride in the presence of aluminium chloride in the conventional Friedel-Crafts solvents of dichloromethane and 1,2-dichloroethane no yield of desired product was obtained. Instead black tars resulted.

Clearly there exists a need for a commercially feasible synthesis of the compounds of the formula (I) and that need is not met by use of conventional methods of performing a Friedel-Crafts reaction.

We have now found a process that gives unexpectedly high yields and is commercially feasible on a plant scale.

According to the present invention there is provided a process for preparing a compound of the formula (I) which comprises reacting a compound of the formula (II) with a compound of the formula (III):

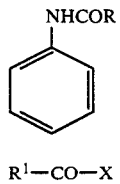
(II)

$R^1$—CO—X (III)

in which R is $C_{1-4}$alkyl; $R^1$ is $C_{1-4}$alkyl or $C_{1-4}$haloalkyl and X is chloro or bromo, in the presence of aluminium chloride characterised in that the solvent comprises trichlorobenzene.

Suitably R is ethyl, preferably R is methyl.

Suitably $R^1$ is $C_{1-4}$alkyl. More suitably, $R^1$ is methy or ethyl.

Preferably $R^1$ is $C_{1-4}$haloalkyl. More preferably $R^1$ is 1-chloroethyl or 1-bromoethyl.

Suitably the reaction is performed at a temperature of about 60°–150° C., more suitably about 80°–120° C. and preferably at about 100° C.

The reaction solvent can be the 1,2,3-isomer, the 1,2,4-isomer or the 1,3,5-isomer of trichlorobenzene or can be a mixture thereof. Preferably the reaction solvent is 1,2,4-trichlorobenzene.

Aluminium chloride can be used in any form and quantity known to be suitable for Friedel-Crafts reactions. Suitably 2–4 mole equivalents of aluminium chloride relative to the compound of the formula (II) are used, for example about 3 moles.

In the compound of the formula (II), X is preferably chloro, so that an acid chloride is reacted. Suitably 1–5 mole equivalents of the compound of the formula (II) are used, conveniently about 1.5 mole equivalents.

The product is isolated from the reaction mixture in conventional manner, for example by quenching and extracting the organic material from the mixture of organic and inorganic material.

The following Examples serve to illustrate this invention.

EXAMPLE 1

Preparation of p-acetamidopropiophenone

Acetanilide (13.94 g), propionyl chloride (14.31 g) and 1,2,4-trichlorobenzene (100 ml) were warmed to 60° C. and aluminium trichloride (40.0 g) was added over 15 minutes. The mixture was heated at 100° C. for 90 minutes, cooled at 40° C. and ethanol (200 ml) was added dropwise keeping the temperature below 60° C. by means of an ice-water bath. After stirring for 30 minutes at 40° C. a homogeneous system was obtained. This was quenched with water (100 ml) at 25°–30° C. and stirred for 15 minutes. Dichloromethane (300 ml) and water (200 ml) were added and the organic layer was separated and washed with water (2×200 ml). The organic layer was evaporated to about half-volume (about 150 ml), and petroleum ether (60° C.–80° C.) (150 ml) was added at 50° C. A solid precipitated and was collected after 60 minutes of stirring to afford p-acetamidopropiophenone (15.12 g; 79%), m.p. 169°–70° C.

EXAMPLE 2

Preparation of 4-Acetamido-α-bromopropiophenone

Bromopropionyl bromide (168 g) was added at 70° C. to a stirred mixture of acetanilide (100 g) and aluminium trichloride (300 g) in 1,2,4-trichlorobenzene (500 ml) so that the temperature did not exceed 80° C.

The mixture was stirred for a further 30 minutes at 80° C., cooled to 60° C. and methanol (100 ml) added slowly with cooling to keep the temperature below 70° C., followed by cautious addition of water (1 liter).

On cooling, the product crystallised out of the organic layer and dichloromethane was added to re-dissolve it. The organic layer was separated, washed with water (twice), aqueous sodium bicarbonate, dried (MgSO$_4$), filtered and concentrated at 60° C. Petroleum ether (60°–80° C.) was then added to crystallise a solid which was collected and dried to give 4-acetamido-α-bromopropiophenone (186 g; 93%), m.p. 107°–112° C.

EXAMPLE 3

Preparation of 4-acetamido-α-chloropropiophenone

Chloropropionyl chloride (9.9 g) was added to a stirred mixture of acetanilide (10 g) and aluminium trichloride (30 g) in 1,2,4-trichlorobenzene (50 ml). The mixture was stirred for 30 minutes at 75°–80° C., cooled to 60° C., methanol (10 ml) added followed by cautious addition of water (100 ml). On cooling, the product crystallised out of the organic layer and dichloromethane (50 ml) added to re-dissolve it. The separated organic layer was washed with water (twice), dried (MgSO$_4$), filtered and concentrated by warming. Petroleum ether (60°–80° C.) was then added to crystallise a solid which was collected, washed with petroleum ether and dried to give 4-acetamido-α-chloropropiophenone (15.03 g; 90%), m.p. 109°–112° C.

What is claimed is:

1. A process for preparing a compound of the formula (I):

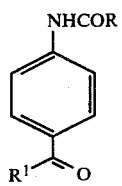

in which
R is C$_{1-4}$alkyl; and
R$^1$ C$_{1-4}$alkyl or C$_{1-4}$haloalkyl
which comprises reacting a compound of the formula (II) with a compound of the formula (III):

in which R is C$_{1-4}$alkyl; R$^1$ is C$_{1-4}$alkyl or C$_{1-4}$haloalkyl and X is chloro or bromo, in the presence of aluminium chloride characterised in that the solvent comprises trichlorobenzene.

2. A process according to claim 1 wherein the solvent is 1,2,4-trichlorobenzene.

3. A process according to either claim 1 or claim 2 wherein R is methyl.

4. A process according to any one of claims 1 or 2 wherein R$^1$ is ethyl.

5. A process according to any one of claims 1 or 2 wherein R$^1$ is 1-chloroethyl or 1-bromoethyl.

6. A process according to any one of claims 1 or 2 wherein X is chloro.

7. A process according to any one of claims 1 or 2 wherein the temperature is between 80°–120° C.

8. A process according to any one of claims 1 or 2 wherein 2–4 mole equivalents of aluminium chloride are used, relative to the compound of the formula (II).

9. A process according to claim 1 or claim 2 wherein R$^1$ is 1-chloroethyl or 1-bromoethyl and X is chloro.

10. A process according to claim 9 wherein the temperature of the reaction is between about 80° and about 120° C.

11. A process according to claim 10 wherein about 2 to about 4 mole equivalents of aluminum trichloride are used, relative to the compound of the formula (II).

* * * * *

UNITED STATES PATENT AND TRADEMARK OFFICE
CERTIFICATE OF CORRECTION

PATENT NO. : 4,677,228

DATED : June 30, 1987

INVENTOR(S) : Brian M. Adger

It is certified that error appears in the above-identified patent and that said Letters Patent is hereby corrected as shown below:

At column 3, line 35, correct to read as follows:

$R^1$ is $C_{1-4}$alkyl or $C_{1-4}$haloalkyl

Signed and Sealed this

Tenth Day of November, 1987

Attest:

DONALD J. QUIGG

*Attesting Officer*  *Commissioner of Patents and Trademarks*